United States Patent [19]
Sauton et al.

[11] Patent Number: 6,051,752
[45] Date of Patent: Apr. 18, 2000

[54] GENETIC FACTOR RESPONSIBLE FOR A DEFECTIVE ENDOSPERM PHENOTYPE IN SEEDS, PLANTS COMPRISING SAID FACTOR AND THEIR USE IN HYBRIDIZATION PROCESSES

[75] Inventors: Annie Sauton; Daniel Gabillard, both of Ledenon; Yves Gonon, Generac, all of France

[73] Assignee: Petosluis Recherche France, Nimes, France

[21] Appl. No.: 08/687,502

[22] PCT Filed: Jan. 20, 1995

[86] PCT No.: PCT/EP95/00213

§ 371 Date: Jul. 19, 1996

§ 102(e) Date: Jul. 19, 1996

[87] PCT Pub. No.: WO95/19696

PCT Pub. Date: Jul. 27, 1995

[30] Foreign Application Priority Data

Jan. 21, 1994 [EP] European Pat. Off. ............. 94400133

[51] Int. Cl.$^7$ ................................. A01H 5/00; A01H 1/00
[52] U.S. Cl. .......................... 800/276; 800/277; 800/295; 800/298; 800/300; 800/308; 800/307; 800/310
[58] Field of Search ..................................... 800/200, 230, 800/250, 277, 295, 298, 300, 308, 307, 310; 47/58, DIG. 1, DIG. 19

[56] References Cited

U.S. PATENT DOCUMENTS 4,513,532  4/1985  Muirhead, Jr. et al. .

OTHER PUBLICATIONS

Welsh. Fundemental of Plant Genetics and Breeding. 1985.
Sauton. Scientia Horticulturae. 1988. vol. 35: 71–75.
Ottaviano et al. Theore. Appl. Genetics. 1988. vol. 75: 252–258.
Sauton and de Vaulex. 1987. Agronomie. vol. 7: 141–148.
Sauton. Eucapia Cucurbits–31/05,01–02/06–Montavet, France. 1989.
Sauton et al. Acta Horticulturae. 1989. vol. 253: 131–135.
Sauton et al., Use of Soft X–ray Technique To Detect Haploid Embryos In Immature Seeds Of Melon, Acta Horticulture 253, 1989, pp. 131–135.
Ottaviano et al., Gametophytic expression of genes controlling endosperm development in maize, International Journal of Breeding Research and Cell Genetics, vol. 75, No. 2, 1988, pp. 252–258.
Sauton, Effect of Season and Genotype on Gynogenetic Haploid Production in Muskmelon, *Cucumis melo* L., *Scientia Horticulturae*, 35, 1988 pp. 71–75.
Mayo, *The Theory of Plant Breeding*, Clarendon Press, 1980, pp. 193–195.
Sauton et al., Obtention de plantes haploïdes chez le melon (*Cucmis melo* L.) par gynogenése induite par du pollen irradié, *Agronomie*, 1987, 7(2), pp. 141–148.
Allard, *Principles Of Plant Breeding*, 1960, pp. 424–426.
Sauton, Doubled Haploid Production In Melon, Eucarpia Cucurbits, 1988, pp. 119–128.
Meinke, Embryo–lethal mutants of *Arabidopsis thaliana*: analysis of mutants with a wide range of lethal phases, Theoretical and Applied Genetics, vol. 69, 1985, pp. 543–552.

*Primary Examiner*—Lynette R. F. Smith
*Assistant Examiner*—Ousama M-Faiz Zaghmout
*Attorney, Agent, or Firm*—Rockey, Milnamow & Katz, Ltd.

[57] ABSTRACT

The invention relates to a genetic male gametophytic factor capable, when expressed, of conferring a defective endosperm phenotype to seeds, said seeds being unable to germinate on their own. The invention also relates to the use of plants or part of plants comprising said factor for carrying out processes for obtaining hybrid seeds and plants.

16 Claims, 4 Drawing Sheets

GENETIC FACTOR RESPONSIBLE FOR A DEFECTIVE ENDOSPERM PHENOTYPE IN SEEDS, PLANTS COMPRISING SAID FACTOR AND THEIR USE IN HYBRIDIZATION PROCESSES

FIELD OF THE INVENTION

The present invention relates to a genetic male gametophytic factor responsible for a defective endosperm phenotype in seeds. The invention also relates to plants comprising the said factor, especially those obtained from such seeds and the use of such plants in processes for obtaining hybrid seeds and hybrid plants.

BACKGROUND OF THE INVENTION

In the majority of angiosperms, during the seed development, after fertilization, reserves accumulate in a particular tissue, called endosperm, which is generally triploid.

The endosperm will provide the embryo for feeding. It results from the fusion of one of the two spermatic nuclei (male) with both polar nuclei of embryo sac (female).

This endosperm divides very actively, but in a very peculiar manner; nuclei are not separated by cell walls, but are placed on the periphery of the embryo sac forming a coenocytic mass, which covers sac walls and progresses little by little towards inside.

Later on, and depending on species, this mass will or not segment and transform into a true cellular tissue. In the embryo sac, the embryo develops, from globular state to its final state through various intermediate states, which depend on the species (e.g. in melon: cordiform then torpedo and finally cotyledonous states). In the meantime, endosperm grows at the expense of nucellus, which resorbs progressively, in such a way that in mature seed, endosperm gets in direct contact with teguments.

But in some cases, endosperm disappears progressively and reserves accumulate then into cotyledons which become thicker and puffed, and fill in all the seed.

The seed is then designated as "non endospermic". This type of seed is met in numerous botanical families, as Cruciferae (e.g. brassicas, rape seed), Papillonaceae (e.g. legumes as bean, pea, soyabean), Cucurbitaceae (e.g. melon, cucumber, squash), Compositae (e.g. sunflower).

In opposite, cereals (including maize), solanaceae, and many other cultivated plants have endospermic seeds. In endospermic seeds, reserves which remain within endosperm instead of accumulating into cotyledons are directly mobilized from endosperm during germination process.

It is already known that physicochemical gradients inside endosperm (Ryczkowski, 1967) and nutrients provided to the embryo (Monnier, 1980) are decisive for a normal morphogenetic expression which will lead to autotrophy.

It has also been demonstrated that chemically induced mutations affecting endosperm development could result in a more or less strong embryo lethality in maize (Neuffer and Sheridan, 1980) or in Arabidopsis (Meinke, 1985).

It is also known that, in higher plants, there are a large number of genes expressed during the male gametophytic phase (i.e. the haploid development phase in which male reproductive cells called "male gametes" differentiate). A large portion of these genes are also expressed in the sporophytic phase (i.e. the phase corresponding to the diploid development till the next gametophytic phase, of the organism issued from a zygote—or egg—which results from the fusion of male and female gametes during fertilization) (Mascarenhas et al. 1986).

It has also been observed that components of pollen development and function show positive correlations with endosperm development (Mulcahy 1971, Ottaviano et al., 1980), and that some alleles determining defective endosperm in maize (Ottoviano et al. 1988) and lethal embryo in Arabidopsis (Meinke 1982, 1985, Meinke and Baus 1986) are expressed in the male gametophyte. In this last case, the detection of defective endosperm mutant genes affecting the male gametophytic generation is mainly based on distortion from the expected mendelian segregation, and on heterogeneity between ovary sectors.

DETAILED DESCRIPTION OF THE INVENTION

The present invention relies on the identification made by the inventors of a genetic male gametophytic factor in plants, said factor being susceptible to correspond to one or several nucleotide sequence(s), and more particularly to one or several gene(s), and said factor being responsible for the defective endosperm phenotype of seeds borne by the fruits resulting from fertilization by the pollen of those plants.

Thus the present invention provides for the first time processes for isolating this genetic male gametophytic factor in plants, or in parts of plants, and controlling its expression, as well as for isolating plants, or parts of plants, carrying such genetic male gametophytic factor, and more particularly seeds characterized by said defective endosperm phenotype.

The present invention also provides processes for transferring this genetic male gametophytic factor from plants into other plants.

The present invention also provides new tools for the study of seed maturation mechanism, and consequently for the study of seed quality.

The present invention also provides new tools for the study of artificial seed production where seed maturation mechanism is the major limiting factor for successful technology development.

The invention also provides a new process for obtaining hybrid seeds and plants, carrying predetermined characteristics, the hybridization technique being based on the use of the genetic male gametophytic factor described above, which use is comparable to the one of a male sterility system (such as described in the French patent n° 2 542 569, or in the UK patent application n° 2 211 205). This hybridization technique can replace existing techniques like emasculation, chemical treatments, cytoplasmic or genetic male sterilities, self incompatibility.

Thus the present invention relates to a genetic male gametophytic factor derived from non-endospermic seeded plants, which genetic factor is capable, when expressed, of conferring a defective endosperm (De) phenotype to seeds, these defective endosperm seeds, also called deficient seeds when extracted from mature fruits, being unable to germinate on their own in soil, or any classical seed germination substrate used in agriculture and horticulture for plant production or in laboratories for seed germination tests (such as substrates described in Seed Science and Technology, Proceedings of the International Seed Testing Association, International Rules for Seed Testing, 1993, Annex to Chapter 5, p. 148–150).

If necessary, said deficient seeds extracted from mature fruits, are treated according to current seed production procedures known by the man skilled in the art, before sowing. For example, said seeds are dried in the case of melons and other fruits vegetables, in order to obtain good storable seeds.

By defective endosperm seeds, one should understand that it corresponds to seeds in which the defective endosperm character can be detected from early developmental stage, and which are not able to evolve into normal mature seeds in vivo.

For instance, this early developmental stage where said defective endosperm character can be detected in melon seeds, corresponds to cotyledonous stage.

In other words, one should understand that said defective endosperm seeds correspond to immature seeds, not only when considered at their early developmental stage, but also when considered at their final developmental stage corresponding to the stage of formation of a normal mature seed.

However, for simplification purpose, the defective endosperm seeds (or De seeds), according to the invention will be designated in the following by the expression "deficient seeds" (which can be obtained from mature fruits) by opposition to "normal mature seeds", when considered at their final developmental stage, or by the expression "developing deficient seeds" (which can be obtained from immature fruits) by opposition to "normal immature seeds".

Developing deficient seeds bearing a De phenotype according to the invention, are more particularly characterized in that:
they are unable to evolve in vivo into normal mature seeds which embryo presents superposed and puffed cotyledons,
they evolve in vivo into deficient seeds according to the invention, which embryo presents spread and thin cotyledons, and which as already mentioned above, are unable to germinate on their own in soil, or on any classical seed germination substrate.

The genetic male gametophytic factor according to the invention, is more particularly characterized in that it is expressed in defective endosperm seeds such as those obtained from fruits resulting from the crossing of female parent plants which are homozygous or heterozygous for said factor, or which do not comprise said genetic factor, with male parent plants which are homozygous or heterozygous for said genetic factor.

In case the male parent plant, cited above, is homozygous, 100% of the seeds formed in the fruits will be De seeds.

In case the male parent plant cited above, is heterozygous, a significant part of the seeds formed in the fruit will have normal phenotype, i.e. will correspond to normal seeds.

For illustration purpose, the theoretical proportions of De seeds obtained in the crossing process described above, when the male parent plant is heterozygous, are the following:

female plants homozygous for said factor crossed with male plants heterozygous for said factor: 50% of De seeds are obtained,
female plants heterozygous for said factor crossed with male plants heterozygous for said factor: 50% of De seeds are obtained,
female plants which do not comprise said factor crossed with male plants heterozygous for said factor: 50% of De seeds are obtained.

In some experimental conditions, observed rates might seem to differ from these theoretical proportions, due to the incidence of following factors:
the current formation of "empty seeds",
the current formation of mis-filled seeds influenced by environmental conditions,
pollen competition as will be described below.

Adequate correction is necessary, based on the rates of empty seeds and mis-filled seeds observed among normal mature seeds, to meet the above-mentioned theoretical percentages.

The genetic male gametophytic factor according to the invention is also more particularly characterized in that it derives from non endospermic seeded plants, such as Cucurbitaceae, in particular from melon species (*Cucumis melo L*), for instance, from melon plants issued from melon seeds designated RS 14685 and deposited at the NCIMB in Aberdeen, England, under the number 40602 on Dec. 1st, 1993.

Based on the processes and techniques according to the invention, said genetic male gametophytic factor can be identified in other non endospermic seeded plants susceptible to contain said factor, as for instance in Cucurbitaceae (e.g. cucumber, squash, watermelon), in Cruciferae (e.g. brassicas, rape seed, radish, Arabidopsis), in Papillonaceae (e.g. legumes as bean, pea and soyabean), in Compositae (e.g. sunflower, endive, lettuce).

Based on the informations disclosed in the present application, one skilled in the art can as well reproduce the invention by using other known similar techniques and processes.

The invention also relates to a process for obtaining non endospermic seeded plants comprising a genetic male gametophytic factor according to the invention, said process being carried out by combining a double haploid technology, as described for instance in melon, according to Sauton 1988a and 1988b, with a screening method for identifying those plants comprising said genetic male gametophytic factor. As those plants comprising said factor are capable, when used as pollen donor in a crossing, to generate fruits comprising De seeds, said screening method can be performed by observation of said De seeds within the progenies of the doubled haploid plants obtained according to the double haploid technology mentioned above, for instance by X-ray radiography or any equivalent non destructive imaging method, enabling to visualize embryo inside seeds.

In a preferred embodiment, the above-mentioned process according to the invention comprises:
the production of haploid plants from source-plants capable of comprising a genetic male gametophytic factor according to the invention, by pollination of the said source-plants with irradiated pollen from said source-plants (or pollen of any compatible genotype), such as described for instance in melon according to Sauton and Dumas de Vaulx 1987 and Sauton 1988a,
the chromosome doubling of haploid plants obtained above in order to obtain doubled haploid plants, as for instance in melon by colchicine treatment according to Sauton 1988b, the self-fertilization of doubled haploid plants obtained above, the screening of those doubled haploid plants comprising the genetic male gametophytic factor by observation of developing deficient seeds, or deficient seeds, respectively extracted from immature or mature fruits (depending on the chosen screening method) issued from self-fertilization of doubled haploid plants obtained above, by X-ray radiography according to Sauton et al 1989, which allows the detection of defective endosperm developing seeds characterized by their embryos with spread and thin cotyledons, or by any equivalent screening method such as direct sowing in soil, seed dissection, floating techniques in water or in a gradient of liquid, or of fluid, or such as methods using other imaging technologies (as nuclear magnetic resonance, ultrasound scan, or gamma-ray scan), the recovery of doubled haploid plants comprising the genetic male gametophytic factor, as identified above, among the doubled haploid plants obtained above.

The process for obtaining plants comprising said genetic male gametophytic factor, as described above, may also comprise an additional step of in vitro culture on an appropriate substrate (such as medium without hormons, as described in Murashige and Skoog, 1962) of defective endosperm seeds obtained from fruits of the doubled haploid plants recovered in the last step of the above-mentioned process.

Doubled haploid plants comprising said genetic male gametophytic factor thus obtained, may then be self-fertilized and the defective endosperm seeds obtained from fruits of these plants may be in vitro cultivated in order to obtain the next generation of plants issued from doubled haploid plants comprising said genetic male gametophytic factor, and so on.

By carrying out these repetitive steps, one can maintain the resulting doubled haploid line, defined as the set of inbred individuals, with an absolute genotypical and phenotypical uniformity because of their homozygozity at all loci, which result from conform reproduction of a doubled haploid plant homozygous for said genetic male gametophytic factor. So this process provides a method for reproducing homozygous plants comprising said genetic male gametophytic factor.

The genetic male gametophytic factor may also be maintained in a heterozygous state in normal seeds, either any seed used as host of the genetic male gametophytic factor (which would for instance result from the crossing of any donor mother plant comprising the genetic male gametophytic factor in an homozygous state, with any plant of the same species or of compatible species taken as male), or a specific seed containing in its genome predetermined characteristics (which would for instance result from the crossing of a mother plant presenting predetermined characteristics and comprising the genetic male gametophytic factor in an homozygous state, with an isogenic plant taken as male, isogenic meaning a plant wherein all genes are identical, with the exception of the said factor).

The source-plants capable of comprising a genetic male gametophytic factor according to the invention, and which are used in the process described above, are non endospermic seeded plants, such as described above, in particular Cucurbitaceae, such as melon species, for instance, melon plants issued from melon seeds designated RS14685 and deposited at the NCIMB in Aberdeen, England, under the number 40602 on Dec. 1st, 1993.

By way of illustration, the expression of the genetic male gametophytic factor is stable in any kind of genetic background in melon species; i.e. when transferred several times from one plant progeny to another one, the expression of said factor remains stable.

The invention also relates to a process for obtaining defective endosperm seeds comprising a genetic male gametophytic factor according to the invention, said process being carried out by recovery of said deficient seeds obtained from fruits borne by doubled haploid plants comprising the genetic male gametophytic factor and identified or maintained according to the process described above.

The invention also relates to defective endosperm seeds comprising a genetic male gametophytic factor according to the invention.

Defective endosperm seeds according to the invention are more particularly characterized in that they express the said genetic male gametophytic factor. The defective endosperm seed can either be homozygous or heterozygous for said factor; the factor at least being transmitted by the male gametophyte.

The invention relates more particularly to defective endosperm seeds which are homozygous for the genetic male gametophytic factor, and such as obtained from fruits borne by doubled haploid plants comprising said genetic male gametophytic factor, said doubled haploid plants being obtained by carrying out the process described above.

As already mentioned above, defective endosperm seeds according to the invention, are characterized in that:

they are not able to germinate on their own in soil, or on any classical seed germination substrate, they are unable, when considered at their early developmental stage, to evolve in vivo into normal mature seeds which embryo presents superposed and puffed cotyledons, they evolve in vivo, when considered at their final developmental stage (when the fruit is ripe), into deficient seeds, which embryo presents spread and thin cotyledons.

For instance, the embryo of deficient seeds in melons, has a reduced volume from approximately 2 to 4 fold with respect to the embryo of normal mature seeds in melons.

The invention also relates to normal mature seeds comprising a genetic male gametophytic factor according to the invention, said mature seeds being heterozygous for said genetic factor, and wherein said genetic factor is not expressed, because transmitted only by female gametophyte.

The invention relates more particularly to normal mature seeds according to the invention, such as obtained from fruits of plants resulting from the crossing of female parent plants which are homozygous or heterozygous for said genetic factor, and male parent plants which do not comprise said genetic factor.

The invention also relates to plants, or any part of plants, such as pollen, explant, fruit, plant cells or protoplasts, or any product from plants, comprising a genetic male gametophytic factor according to the invention, these plants, or parts of plants, being homozygous or heterozygous for said genetic male gametophytic factor.

The invention relates more particularly to plants such as obtained by in vitro culture of defective endosperm immature seeds, which are homozygous for said genetic male gametophytic factor, as described above, these plants being characterized in that they are homozygous for said genetic male gametophytic factor.

The invention also relates to plants such as obtained by cultivating normal mature seeds as described above according to the invention, these plants being characterized in that they are heterozygous for said genetic male gametophytic factor.

The invention relates to processes allowing the transfer of the genetic male gametophytic factor comprised in a species of non endospermic seeded plants, to another species of non endospermic seeded plants, which processes being carried out according to genetic transformation techniques, or techniques of cell fusion or protoplast fusion as developed nowadays in the field of plant biotechnology and already realized for other characteristics like virus or herbicide resistances. These techniques will not be remembered here in details, because known from experts in the art.

By way of illustration, cells or protoplasts fusions can be carried out according to methods described in Pelletier and Chupeau, 1984.

The invention relates to cells, and more particularly plant cells, or protoplasts, which have been transformed in order to comprise said genetic male gametophytic factor.

The invention relates more particularly to transformed cells such as obtained by fusion between cells comprising said factor and cells to be transformed in order to comprise said factor (these latter possibly belonging to a species which is different from the species corresponding to the cells comprising said factor used in the fusion process).

The invention also relates to plants or part of plants comprising said genetic male gametophytic factor such as obtained from cells or protoplasts issued from the fusion techniques described above.

The invention also relates to a process for obtaining hybrid mature seeds, the genome of which comprising one (or several) gene(s) coding for one (or several) predetermined characteristics, said process comprising:

crossing a first female parent line, said female line corresponding to plants being homozygous for said genetic male gametophytic factor, as described above, with a second male parent plant which do not comprise the genetic male gametophytic factor according to the invention, at least one of the female or male parent line comprising said predetermined characteristics, the recovery of the seeds from fruits borne by female parent plants, according to current seed extraction methods well known by experts in seed production, if necessary, the screening of normal mature seeds resulting from said crossing, among the defective endosperm seeds corresponding to selfings which might be produced by self pollination of the female plants in the crossing step mentioned above, in particular in open pollination conditions in an isolated production field, said screening being carried out according to any seed cleaning method suited for separation of partly or totally empty seeds from normal mature seeds, such as densimetric table, "clipper" or any method based on specific gravity.

The crossing step in the process described above can be performed by any pollination method suited for the concerned species. In particular for allogamous (i.e. cross pollinated) crops, the described process enables to use open pollination conditions in a production field isolated from unexpected source of pollen (i.e. different from the chosen male parent), the isolation distance depending on the species and being a current parameter for an expert in seed production.

Processes for obtaining hybrid plants and seeds, and which could be used in the frame of the present invention, are more particularly described in Kuckuck et al., 1991.

Different versions of this general process can be adapted, according to, on one hand, the current production practices and equipments available and, on the other hand, the seed quality requirements to be satisfied. For instance, in the second step of the process, extracted seeds are a mixture of normal mature hybrid seed,—which will normally germinate—and deficient seeds corresponding to the selfing of the mother parent, which will be unable to germinate in soil. Depending on the level of seed quality requirements, this mixture can be used for direct sowing or needs to be processed according to the third step of the process.

The invention also relates to hybrid seeds heterozygous for a genetic male gametophytic factor according to the invention, and which comprise predetermined characteristic (s), said hybrid seeds being obtained according to the process described above.

The invention relates more particularly to any hybrid mature seeds susceptible to lead to the production of at least approximately 10% of De seeds per fruit, these fruits being obtained from plants emerged from said hybrid mature seeds and which, when reaching appropriate flowering stage, have been self pollinated in such conditions that any uncontrolled cross pollination is prevented. Detection of the De seeds contained in the fruits borne by the self pollinated plants mentioned above, can be carried out by X-ray radiography according to Sauton et al., 1989, as described above.

Up to 50% of De seeds can be detected in the process described above, if there is no competition between De pollen grains (i.e. pollen bearing the genetic male gametophytic factor), and normal pollen ones. In case of pollen competition (unfavourable to De pollen), about 10% of De seeds can be obtained.

The invention also relates more particularly to hybrid mature seeds susceptible to lead to the production of approximately 75% of De seeds, up to 100%, among fruits resulting from the self-pollination of plants in such conditions that any uncontrolled cross pollination is prevented, said plants being obtained from the in vitro culture of De seeds themselves obtained from fruits resulting from the crossing of plants emerged from said hybrid mature seeds, and taken as male (pollen donor), with a De homozygote plant source taken as female. For instance, in case of melon, said De homozygote source corresponds to melon plants derived according to previously described methods from plants issued from melon seeds designated RS14685 and deposited at the NCIMB in Aberdeen, England, under the number 40602 on Dec. 1st, 1993.

As already mentioned above, detection of the De seeds contained in the fruits borne by the plants mentioned above and issued from selfing, can be carried out by X-ray radiography according to Sauton et al., 1989, as described above.

The invention also relates to hybrid plants, heterozygous for a genetic male gametophytic factor according to the invention, and which comprise predetermined characteristics, said hybrid plants being obtained by cultivating hybrid seeds described above.

The invention will be further described in the detailed description which follows of the obtention of doubled haploid (DH) melons comprising a genetic male gametophytic factor according to the invention.

Figure 1:
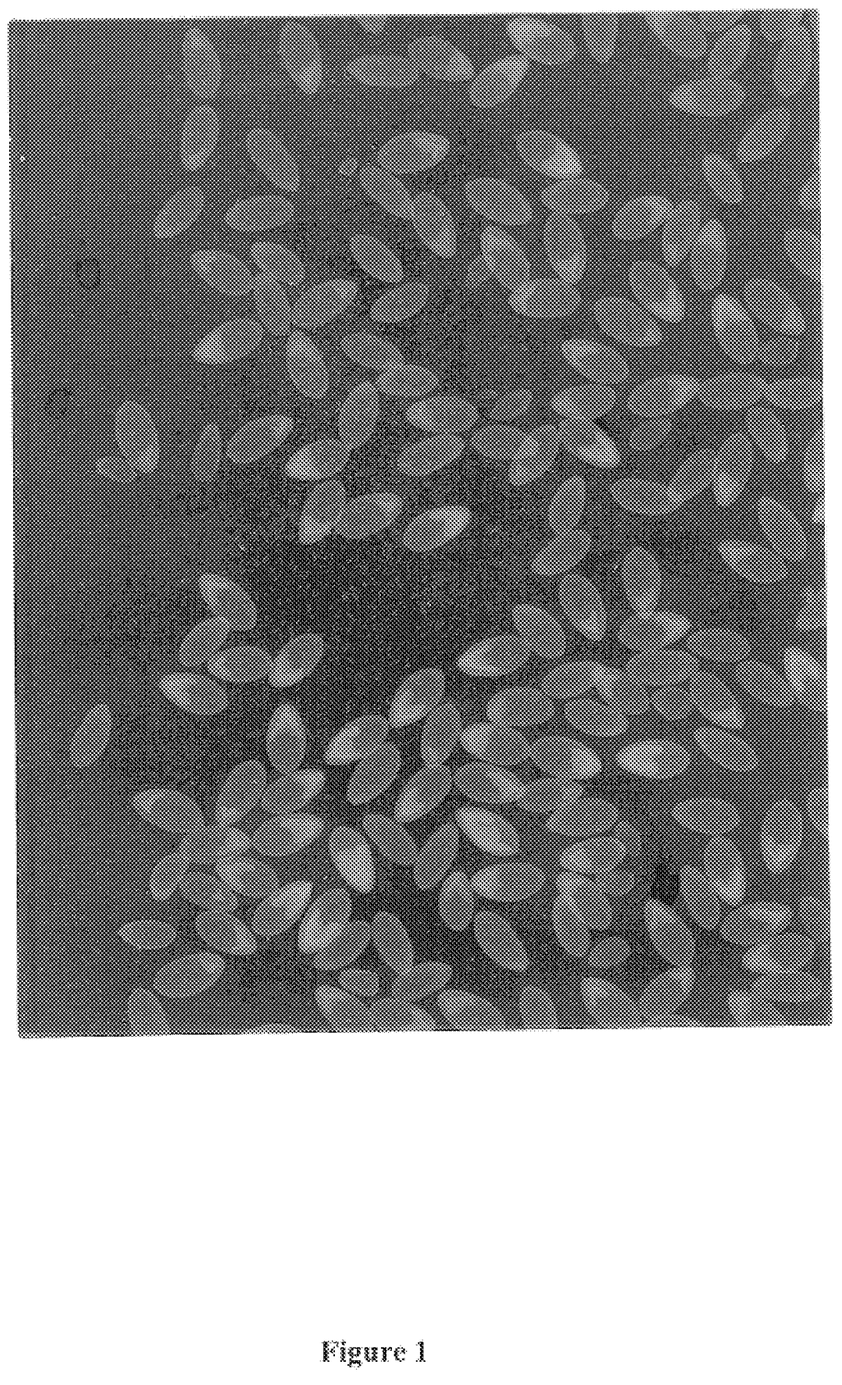
FIG. 1 shows an x-ray of spread and thin cotyledons, a characteristic of a defective endosperm phenotype, in seeds from B69 melon line.
Figure 2:
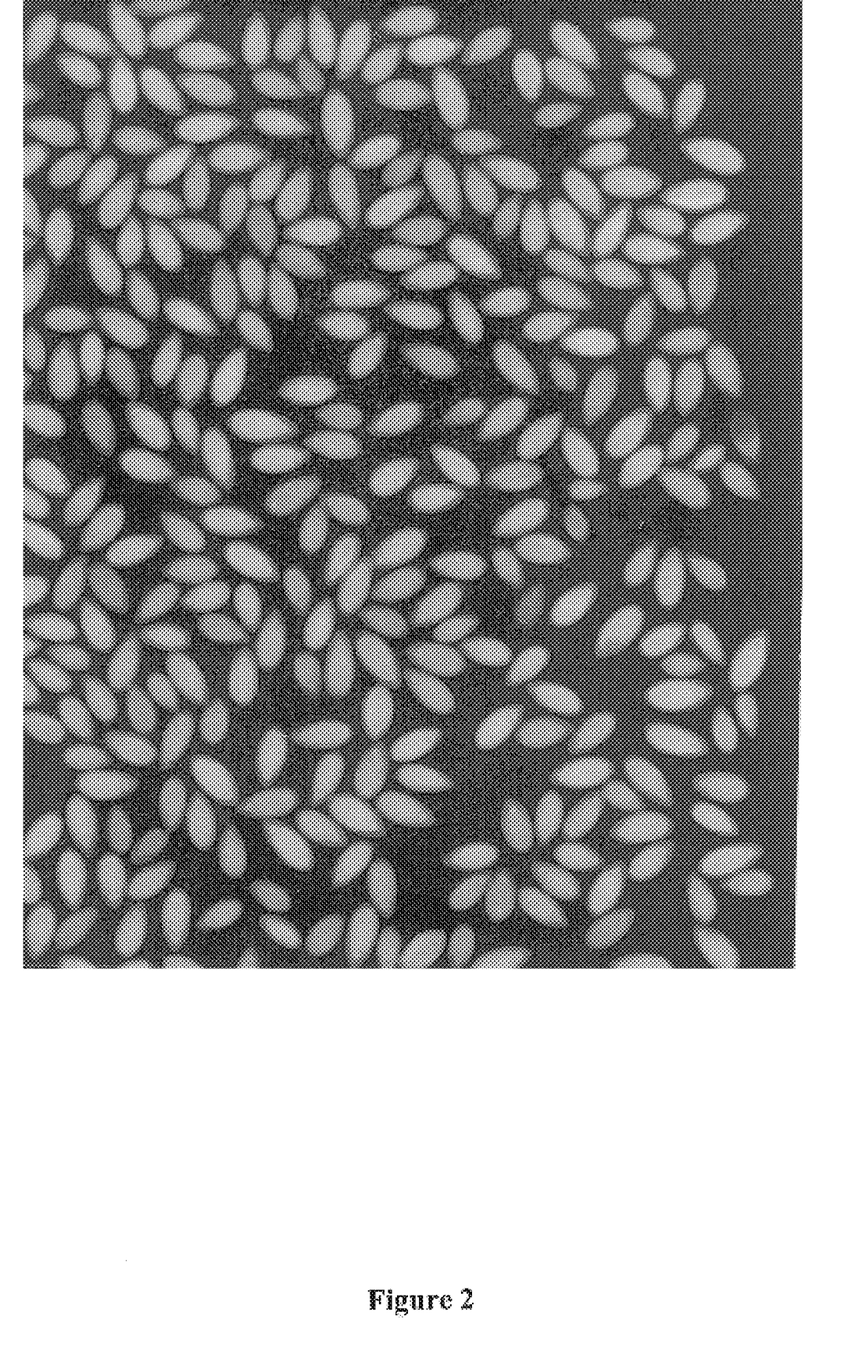
FIG. 2 shows an x-ray of normal melon seeds from the Védrantais melon line (control genotype).
Figure 3:
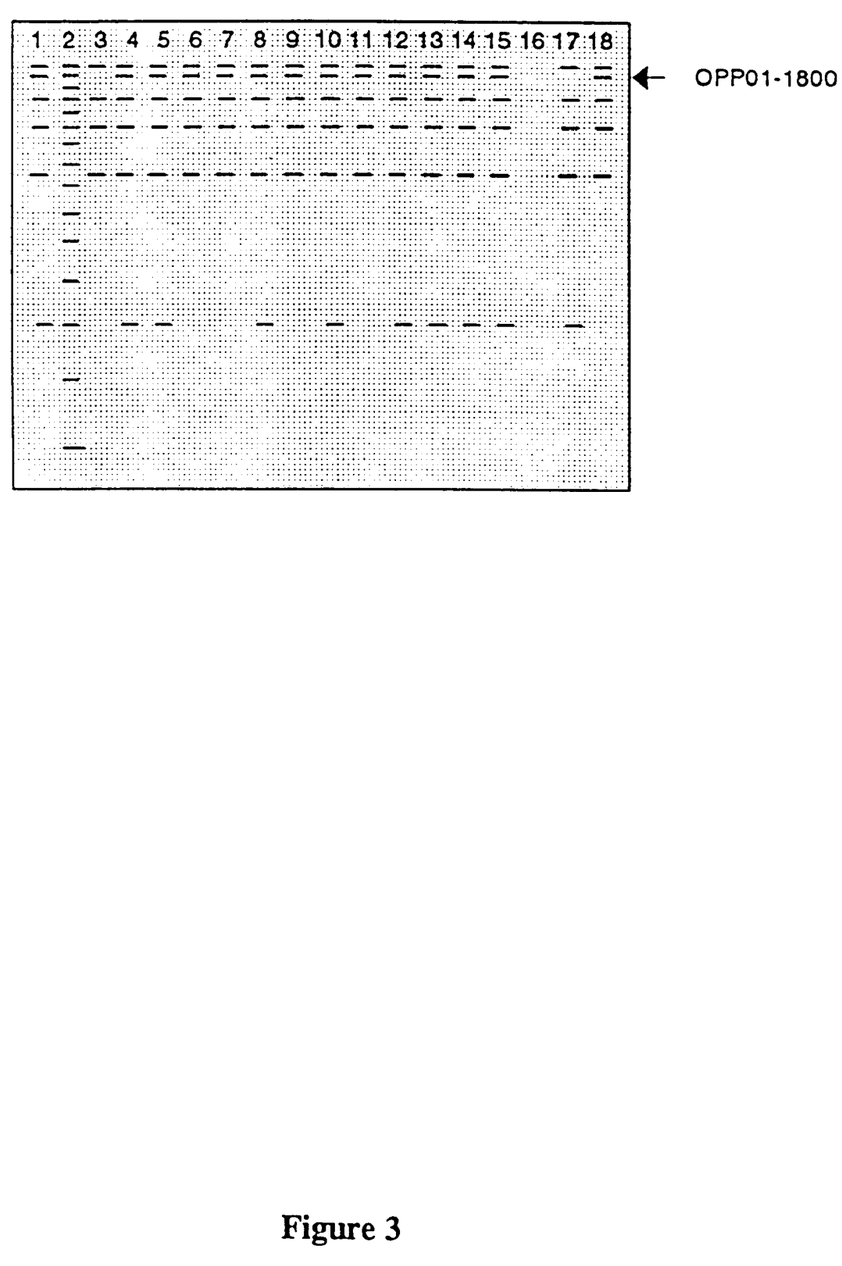
FIG. 3 shows the amplification in an agarose gel of marker OPP01-1800.
Figure 4:
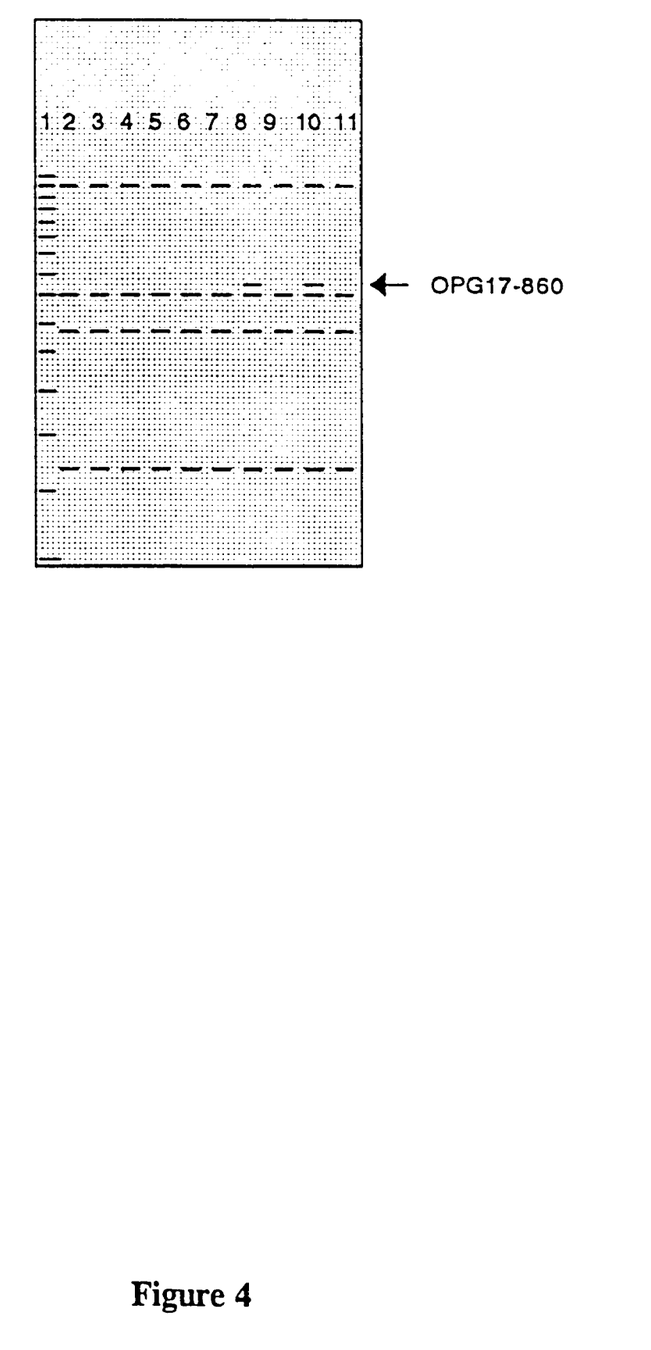
FIG. 4 shows the amplification in an agarose gel of marker OPG17-860.

The invention is illustrated by the following figures:

FIGS. 1 and 2 representing De seeds and normal seeds respectively, of charentais melon (such as visualized by X-ray radiography), FIG. 3 visualizes the OPP01-1800 molecular marker used for detection of female selfings among hybrid seed lots, FIG. 4 represents the OPG17-860 molecular marker used for detection of hybrid seeds among the male selfseed lots.

I Experimentation

In this work, a genetic male gametophytic factor has been identified for the first time in the scope of the process of extraction of doubled haploid (DH) lines in charentais melon.

At the time, the DH technique needed a systematical dissection under sterile conditions of all immature seeds to detect and extract globular and heart shaped haploid embryos resulting from pollination by irradiated pollen for further in vitro culture (Sauton 1988a).

In order to improve the efficiency of this DH method, the inventors tried to detect haploid embryos among immature seeds by using X-ray radiography. Preliminary experiments were required to investigate with X-ray the evolution of normal embryogenesis, in order to adjust the technique of observation at various stages of the embryogenesis.

This experiment has been carried out on the progenies of DH plants obtained from the crossing of two lines, both bred out of charentais melon populations, as is the source designated RS 14685 and deposited at the NCIMB in Aberdeen, England, under the number 40602 on Dec. 1st, 1993.

After in vitro rescue, 15 DH plants were regenerated, transferred out of tube, grown and selfed. Resulting fruits were collected at various stages of developments. All the seeds (including empty seeds) obtained from these fruits were systematically examined with X-ray radiography. A specific attention was paid to observation seed per seed of the obtained films.

Seeds issued from selfings of one particular line called B69 showed a special unknown phenotype, characterized by an abnormal embryogenesis.

The radiography technique used is soft radiography provided by a Faxitron® cabinet X-ray system, Hewlett-Packard model 43805 N; this apparatus provided a radiation shielded enclosure, an instant X-ray capability and high resolution radiographs.

Radiograph papers used were Kodak Industrex 620.

II Process for obtaining DH melons comprising said factor

1. Production of haploid plants

Production of haploid plants is described in details in Sauton and Dumas de Vaulx, 1987.

In summary, haploid plants of muskmelon (*Cucumis melo* L.) are obtained following pollination with irradiated pollen ($Co^{60}$ γ-rays) and in vitro culture of ovules or immature embryos. A culture medium was developed to allow further development of these embryos into plants. An average of 2.5 haploid embryos per 100 seeds was obtained. Increasing the amount of irradiated pollen (using 4 flower buds) led to an improved haploid rate. γ-rays doses higher than 30 Krad (or 300 Gy) were necessary to avoid normal fertilization and to obtain only haploid embryos. All the haploid plants showed maternal phenotype. Haploid embryos were characteristic and different from normal diploid embryos of the same age.

2. Chromosome doubling of haploid plants

Chromosome doubling occurred in 50 per cent of cuttings from haploid plants described above, after submersion in a colchicine aqueous solution at 5 g/l during 2 hours.

3. Self-fertilization of DH plants

Cuttings in which chromosome doubling occurred further to colchicine treatment were transplanted out of tubes into pots under greenhouse conditions suited for rooting. Plantlets were raised till a new transplantation into soil in an insect proof greenhouse. When reaching appropriate flowering stage, plants were self pollinated in conditions preventing any uncontrolled cross pollination. Resulting fruits were harvested when ripe and seeds extracted.

4. Screening of said DH melons by X radiography of seeds.

FIG. 1 represents an X-ray film of De seeds in B69 melon line.

De seeds represented on FIG. 1 show spread and thin cotyledons when compared to normal seeds in melon line represented on FIG. 2.

III Seed development in B69—comparison with a control (normal) genotype.

B69 and Vedrantais (control genotype) plants were self-fertilized and fruits harvested at different periods after pollination. Young ovaries or ovules or seeds were prepared for cytological observations according to protocols already available in literature as those described in Jahier, 1992.

1. Control genotype 5 to 6 days after pollination, a coenocytic endosperm nourished the proembryo. A great part of the nucellus was already digested by the endosperm.

Ovules extracted 13 days after pollination showed a voluminous cellular endosperm enclosing an embryo at the cotyledonary stage with superposed cotyledons.

In normal melon mature seeds, which belong to non endospermic type of seeds, the embryo presented superposed and puffed cotyledons and filled the seed.

2. B69 genotype 7 days after pollination, an apparently normal coenocytic endosperm was present.

13 days after pollination, the normal cellular endosperm was absent; the embryo at the heart to cotyledonous stage presented spread cotyledons and was in some cases surrounded by a degenerating tissue which can be a trace of endosperm or nucellus; the haustorium is present.

B69 mature seeds contained embryos with spread and thin cotyledons which in most of the cases did not fill the seed.

This anomaly in embryo development evidenced in DH B69 is the consequence of an early abortion of the endosperm between 8 to 12 days after pollination. Therefore, the particular B69 seed phenotype can be named defective endosperm (De) seed phenotype.

IV In vitro rescue of De seeds and propagation of De plants

De seeds were extracted from B69 fruits 3 to 4 weeks after selfpollination and embryos cultivated in vitro in the same conditions than those fully described for melon haploid embryos in Sauton and Dumas de Vaulx, 1987.

De plants were propagated in vitro by cuttings according to Sauton 1988b.

De plants could also be propagated in greenhouse using conventional methods of cuttings in soil.

V Selfings of DH B69 line and crossing of DH B69 melons obtained above with a normal line 1. Selfing of DH B69 line 1.1 Characterization and heredity of defective endosperm phenotype.

DH B69 was selfed during 5 generations; seeds observed in each generation showed the same De phenotype. So De character is hereditary with a stable expression.

In order to evaluate the frequency of this phenomenon, 6 B69 mature fruits were harvested; seeds were extracted and prepared for X-ray radiography (Sauton et al., 1989). Radiography study showed 3 types of seeds distributed in 3 classes according to embryo morphology.

Class-1: seed full of a normal embryo characterized by superposed and puffed cotyledons; radiographic image is white.

Class-2: seed partly full of an embryo which has superposed but incompletely developed cotyledons; radiographic image is pale grey.

Class-3: seed partly full of an embryo distinguished by spread and flat cotyledons; radiographic image is grey.

Results of this study, realized in 1989, are summarized in Table 1. In B69 fruits approximately 99% of the seeds contained a class-3 embryo and 0.8% a class-2 embryo.

One normal embryo (class-1), among 2540 embryos recorded, was observed. It might be a contamination by a foreign pollen, or a defect in De character expression.

Class-2 and class-3 embryos were collected separately and cultivated in vitro for germination. Developed plants were transferred in soil and selfed in 1990. In each case, 5 fruits were harvested.

Table 2 gives the data of class 2 and class 3 embryos progeny analysis. Progenies from the 2 classes of embryos are not significantly different ($X^2=0.138$, $0,50<P<0.75$). Therefore, classes-2 and 3 represent 2 levels of De character expression.

Selfprogenies of class-1 and class-3 embryos were compared at the seed level. No significative difference between the 2 progenies was found concerning the number per fruit of embryos belonging to each class described above. Therefore, the class-1 embryos observed at very low frequencies in those experiments (2 cases reported among 4244 observed seeds containing an embryo) represent seeds where the defective endosperm character is present but not expressed.

Consequently, the De character is attested of being transmitted in all B69 seeds. Its expression is almost stable, about 99% of the embryos belong to class-3.

TABLE 1

DISTRIBUTION OF B69 SEEDS

| Fruit | Number of seeds per fruit | Number of empty seeds | Number of seeds with an embryo | | |
|---|---|---|---|---|---|
| | | | Class-1 | Class-2 | Class-3 |
| 1 | 524 | 34 | 0 | 2 | 488 |
| 2 | 431 | 19 | 0 | 7 | 405 |
| 3 | 482 | 38 | 0 | 2 | 442 |
| 4 | 392 | 29 | 0 | 1 | 362 |
| 5 | 404 | 53 | 0 | 0 | 351 |
| 6 | 550 | 70 | 1 | 9 | 470 |
| TOTAL | 2783 | 243 | 1 | 21 | 2518 |

TABLE 2

PROGENY COMPARISON OF SELFED PLANTS
DEVELOPED FROM CLASS 2 AND CLASS 3 EMBRYOS

| Embryo | Fruit | Number of seeds per fruit | Number of empty seeds | Number of seeds with an embryo | | |
|---|---|---|---|---|---|---|
| | | | | Class-1 | Class-2 | Class-3 |
| Class 2 | 1 | 364 | 104 | 0 | 0 | 260 |
| | 2 | 489 | 330 | 0 | 0 | 159 |
| | 3 | 531 | 259 | 0 | 3 | 269 |
| | 4 | 329 | 214 | 0 | 0 | 115 |
| | 5 | 401 | 251 | 0 | 1 | 149 |
| | Total | 2114 | 1158 | 0 | 4 | 952 |
| Class 3 | 1 | 155 | 62 | 0 | 1 | 92 |
| | 2 | 386 | 140 | 0 | 2 | 244 |
| | 3 | 439 | 259 | 1 | 1 | 178 |
| | 4 | 176 | 62 | 0 | 0 | 114 |
| | 5 | 471 | 356 | 0 | 1 | 114 |
| | Total | 1782 | 879 | 1 | 5 | 742 |

TABLE 3

1.2 Seasonal effect on De character expression effect of culture environmental conditions on B69 selfprogenies at the seed level; numbers represent the mean number of seeds per fruit, $X \pm \sigma$ standard deviation. Means sharing the same superscript in a line are not significantly different ($P \geq 0.05$; $N = 8$)

| Number of seeds per fruit | Culture season | | |
|---|---|---|---|
| | Spring | Summer | Autumn |
| Class-1 | $0.1^f \pm 0.3$ | $1.9^e \pm 1.6$ | $0.6^f \pm 1.1$ |
| Class-2 | $0.9^d \pm 1.1$ | $5.0^c \pm 2.2$ | $3.0^{cd} \pm 3.2$ |
| Class-3 | $181.6^b \pm 67.4$ | $431.0^a \pm 95.9$ | $427.5^a \pm 62.1$ |
| Empty | $215.5^C \pm 105.8$ | $191.2^{CD} \pm 138.0$ | $49.1^D \pm 23.8$ |
| Total | $398.1^B \pm 112.3$ | $630.4^A \pm 113.7$ | $480.2^B \pm 77.4$ |

The season (environmental factors) had a highly significant effect on the mean number of each type of seeds obtained in B69 selfprogenies ($P \geq 0.01$, Table 3).

The mean number of all the different seed types containing embryos (every class included) produced per fruit is significantly less important in spring ($182.6^B \pm 68.1$) compared with summer ($437.9^A \pm 97.4$) or autumn ($431.1^A \pm 63.2$), ($F=28.06$, $P=0.00$).

The summer season promotes B69 embryo development: indeed, in summer, the frequency of normal class-1 embryos produced per fruit can reach 1% of total seeds containing embryos, precisely $0.41 \pm 0.34$ whereas it is about $0.15 \pm 0.27$ in autumn and only $0.07 \pm 0.20$ in spring.

2. Crossing of DH B69 with a normal line 2.1 F1 study

DH B69 (Pa) was used as male or female parent in crosses with "Védrantais" (Pb) inbred line with normal phenotype. Selfings of DH B69 and "Védrantais" were used as control. 5 to 6 fruits were harvested from each cross or selfing.

Table 4 reports the data obtained from F1 analysis.

F1 embryos (Pa×Pb) are significantly different from F'1 embryos (Pb×Pa) for their phenotype even if their genotype is the same.

Defective seed character is induced by B69 pollen. The female genotype has no significant effect on De character expression.

TABLE 4

F1 AND F'1 ANALYSIS:

| Generation | Genotype | Total number of seeds | Number of empty seeds | Number of seeds with an embryo | | |
|---|---|---|---|---|---|---|
| | | | | Class-1 | Class-2 | Class-3 |
| Pa | B69 | 2783 | 243 | 1 | 21 | 2518 |
| Pb | Vedrantais (Ved) | 3067 | 281 | 2688 | 96 | 2 |
| F1(Pa × Pb) | B69(♀) × Ved(♂) | 2228 | 412 | 1741 | 72 | 3 |
| F'1(Pb × Pa) | Ved(♀) × B69(♂) | 3679 | 2027 | 0 | 30 | 1622 |

2.2 F2 and test cross study

F1 and F'1 were selfed and Védrantais crossed with F1. Selfing of DH B69 and Védrantais were used as control. 5 to 8 fruits were harvested from each cross or selfing.

Table 5 summarizes the results of the segregation analysis.

The male gamete population produced by F1 or F'1 plants contains theoretically parental type (B69 and Védrantais) and recombined type gametes.

TABLE 5

F2, F'2 AND TEST CROSS ANALYSIS:

| Generator | Genotype | Total Number of seeds | Number of empty seeds | Number of seeds with an embryo | | |
|---|---|---|---|---|---|---|
| | | | | Class-1 | Class-2 | Class-3 |
| Pa | B69 | 3741 | 2037 | 1 | 9 | 1694 |
| Pb | Ved | 3033 | 236 | 2778 | 19 | 0 |
| F2 | (B69 × Ved) × (B69 × Ved) | 3522 | 1309 | 1724 | 382 | 107 |
| F'2 | (Ved × B69) × (Ved × B69) | 5251 | 1554 | 3129 | 437 | 131 |
| Testcross | Ved × (B69 × Ved) | 3397 | 493 | 2648 | 132 | 124 |

Class-2 and class-3 embryos were found in F2, F'2 and testcross therefore B69 type pollen, mixed with normal type pollen (Vedrantais) can induce De phenomenon. If the different types of pollen have an equal fertilizing power (no pollen competition) F2 and testcross analysis were to give relevant informations on the number of genes which controls De character expression.

The factor responsible for this defective endosperm phenotype in melon seeds is hereditary and borne by pollen grains, so can be considered as a genetic male gametophytic factor.

Expression of this genetic male gametophytic factor can be considered as mainly stable as the frequency of cases where this factor is not expressed is always below 1%, in the best conditions for De seed development. The non- expression of the genetic male gametophytic factor could be named De-reverse event.

VI Openfield production of B69 line

28 De vitroplants were acclimatized under fog system, grown in greenhouse until 6 to 7 leaves then planted in late spring in openfield conditions near plants of different genotypes which did not comprise the De factor. De plant development and flowering were normal; male and hermaphrodite flowers were attractive for bees.

The De plants produced an average of 11 fruits per plant, each fruit containing De and normal seeds in various proportions.

Radiographs of seeds collected from fruits produced on normal (non-De) plants showed De seeds among normal seeds, establishing that the De pollen was carried by bees and De male gametophytic factor expressed after transport by bees in the different female/male combinations tested.

VII Use of the De line as a male sterile line in a melon hybrid seed production process The feasibility at pilot industrial scale of melon hybrid seed production process was studied.

1. Propagation of the De line B69

De seeds were collected from selfed fruits of B69 plants and germinated in vitro. De plants were grown then propagated in vitro by microcuttings. 450 vitroplants were acclimatized under a fog system in greenhouse then propagated by cuttings to the extent of 1 000 plants.

These plants were used as female in a pilot hybrid seed production trial.

2. Trial of hybrid seed production 2.1 Protocol

Trial was made under an insectproof plastic tunnel of 640 $m^2$ acreage in June, July and August with 2 plants/$m^2$ and a ratio female/male of 3/1. Plants were arranged on 8 lines, stacked and cultivated according to normal known protocols of culture for the crop in the concerned region (south of France).

3 genotypes were chosen for the trial: B69 used as andromonoecious (i.e. plant with male and hermaphrodite (bisexual or perfect) flowers) male sterile female (864 plants), 930921 gynoecious (i.e. plant bearing only female flowers) control female (32 plants) and 921180 andromonoecious male (304 plants). One male plant was intercalated every 3 female plants in a zigzag device; 4 gynoecious plants were distributed per line: 2 at the ends and 2 in the middle of each line. Near each gynoecious plant, one B69 plant was numbered (32 in total). One hive was introduced in the middle of the tunnel when female flowering started.

2.1.1 Fruit harvest

B69 female genotype.

3 to 4 weeks after bees introduction, 10 fruits were taken at random and seed set controlled using X-ray radiography.

Remaining fruits were harvested at mature stage when peduncle came off the fruit very easily. 4 harvests were made in 2 weeks; at each harvest, 20 fruits were randomly sampled for hand seed extraction, the other fruits being used for industrial seed extraction and cleaning.

For the 32 numbered plants, 1 fruit per plant was collected for hand seed extraction; the other fruits produced on these plants were included in other harvests.

930921 gynoecious genotype:

1 fruit from each numbered plant was taken for hand seed extraction.

921180 male genotype:

Seeds of the male line can be harvested on the male plants as the andromonoecious B69 female line is considered as male sterile.

Fruits were harvested at mature stage when peduncle came off the fruit very easily. 3 harvests were made in 2 weeks; at each harvest, 20 fruits were randomly sampled for hand seed extraction, the other fruits being used for industrial seed extraction and cleaning.

2.1.2 Seed extraction and cleaning

Hand seed extraction:

All seeds, i.e. full (normal), partly filled (De) and empty seeds, were extracted from fruits, washed, partly dried and disposed for X-ray exposure as described in Sauton et al., 1989.

Industrial seed extraction and cleaning

The current seed extraction and wet cleaning method was applied aiming at recovering all full seeds. During humid process stage, for each harvest, a sample of floating seeds was kept for radiography.

Seeds were dried then cleaned in order to achieve separation of full from empty and partly filled seeds. Cleaning was applied by successive runnings of the seed lot through a screen separator, an air column and an indented cylinder as commonly used in seed cleaning processes. The cleaning protocol was as follows:

for seeds produced on B69 genotypes, 3 runnings in the screen separator (steps 1 to 3), using successively a 2.5L screen, a 3.25R screen then ventilation; for seeds yielded on 921180 male genotype, one more running with screen 1.4L was necessary before ventilation (so steps 1 to 4);

3 runnings in the air column for B69 (step 4 to 6), only 2 runnings for 921180 (steps 5 and 6);

2 runnings in the indented cylinder for both genotypes (steps 7 and 8).

At each cleaning process step, for each harvest, all the waste was kept; a sample of each loss and of each cleaned seed lot was taken off to be radiographied.

2.1.3 Radiographs analysis

On each radiograph were evaluated the number of normal seeds (NBGNR), the number of De seeds (NBGDE) and the number of empty seeds (NBGVI). Numbers were calculated for each fruit or sample. Variance analyses (Statitcf software) were applied to look at harvest date or experimental design effects (line or place on line effects).

2.2 Results 2.2.1 Seed lots obtained from hand seed extraction

Seed set control on immature fruits

Radiographs of 10 fruits randomly sampled among B69 fruits showed correct and homogeneous seed set attesting that bees were working normally.

Harvest date effect:

4 or 3 dates of harvest, 4 variables studied:

NBGNR, number of normal seeds per fruit,

NBGDE, number of De seeds per fruit,

NBGVI, number of empty seeds per fruit,

NBGTT=NBGNR+NBGDE.

On B69 De genotype, there was no significant effect of the harvest date whatever the studied variable as illustrated in Table 6 for the normal seeds per fruit.

TABLE 6 effect of the harvest date on the mean number ($\overline{X} \pm \sigma$, standard deviation) of normal seeds recorded per fruit in B69

| Harvest date | NBGNR ($\overline{X} \pm \sigma$) |
|---|---|
| 04/08 | 85 ± 43.6 |
| 08/08 | 79.2 ± 54.4 |
| 11/08 | 112.2 ± 49.9 |
| 19/08 | 111.2 ± 101.8 |

The mean number of hybrid seeds produced per fruit on the De line was about 100.

In 921180 male genotype as shown in Table 7, was observed a highly significant effect of the harvest date on the number of normal seeds per fruit (NBGNR: P(F)=0.014), and the number of total seeds containing an embryo (NBGTT: P(F)=0.003).

TABLE 7 effect of the harvest date in the male genotype on NBGNR and NBGTT variables

| Variable | Harvest date | $\overline{X} \pm \sigma$ | Group |
|---|---|---|---|
| NBGNR | 08/08 | 496.8 ± 130.2 | A |
|  | 11/08 | 476.3 ± 101.1 | A |
|  | 19/08 | 391.8 ± 115 | B |
| NBGTT | 08/08 | 560.9 ± 127.5 | A |
|  | 11/08 | 535.1 ± 88.4 | A |
|  | 19/08 | 440.6 ± 115.8 | B |

The quantity of normal pollen grains which have fertilized the 921180 ovules was less important at the end of the culture period (last harvest date) whereas the quantity of De pollen grains was the same (P(F)=0.705).

This is in agreement with the observation that 921180 male flowering ended 1 week earlier than B69 De genotype one.

Consequently, choosing a prolific flowerer as pollen donor and adjusting the maximal period of fruit set on the De female to the period of male full flowering will increase the hybrid seed yield.

Experimental design effect

From the B69 and 930921 gynoecious plants which were numbered in the tunnel, it was possible to look at line or place on line effects.

There was no line significant effect on the 4 studied variables in the 2 genotypes.

There was no significant effect of the place on line in De genotype for all studied variables.

However, in gynoecious genotype, a highly significant effect of the place on line was observed for the number of normal seeds per fruit (NBGNR: P(F)=0.011) and the number of total seeds with embryo (NBGTT: p(F)=0.029) as evidenced in Table 8 but no effect on the number of De seeds per fruit (NBGDE: (P(F)=0.51).

TABLE 8

Effect of the plant place on line in the gynoecious genotype on NBGNR and NBGTT variables

| Variable | Place on line | $\overline{X} \pm \sigma$ | Group |
|---|---|---|---|
| NBGNR | End | 555.3 ± 206.7 | A |
|  | Middle | 378.1 ± 145.6 | B |
| NBGTT | End | 897.3 ± 144.5 | A |
|  | Middle | 769.3 ± 162.8 | B |

This indicates that a larger quantity of 921180 pollen grains has fertilized the ovules of the gynoecious genotype at the tunnel ends compared with the tunnel middle.

This kind of experimental design effect is well known by production experimenters and could be taken into account for further trials on hybrid seed yield improvement when pollinations are done by bees.

Once more, effects that are evidenced with normal pollen grains are not noticed with De pollen; this could be due to the availability of limited quantity of normal pollen compared with De pollen.

Pollen competition evaluation

In this experiment, 787 B69 plants were cultivated until fruit production and 304 male 921180 plants were used as normal pollen donors. Moreover, the production of male flowers evaluated per day and per plant was 9.7±1.9 on De plants and 8.4±2 on 921180 plants. Therefore, the amount of De pollen available was 3 times higher compared with normal pollen one.

Considering equal attractiveness of De and 921180 male flowers for bees and equable transport of pollen grains, the expected frequencies of De seeds and normal seeds per fruit should have been respectively 75% and 25%.

On gyneocious 930921 genotype, only 43% of the hand extracted seeds were De seeds, evidencing a pollen competition between De and 921180 pollen grains, 30% of the De pollen being eliminated in that competition.

Andromonoecious character effect on success of crossfertilization.

Comparison of seed frequencies observed on the 2 andromonoecious genotypes De and 921180 with the gyneocious ones showed a difference of 30% in favour of self-pollen grains (Table 9). This can be due to extra addendum of selfpollen coming from proper anthers of the pollinated andromonoecious flower.

TABLE 9

Effect of anthers in flowers pollinated by the same population of pollen grains on observed seeds frequencies ($\overline{X} \pm \sigma$)

| Seed frequencies (%) | Type of seed | Anthers absence 930921 geno. | presence De genotype | 921180 geno. |
|---|---|---|---|---|
| expected | normal | 25 | 25 | 25 |
|  | De | 75 | 75 | 75 |
| observed | normal | 56.97 ± 20.4 | 25.3 ± 18.1 | 88.94 ± 12.59 |
|  | De | 43.03 | 74.7 | 11.06 |

Combination of pollen competition and andromonoecious character effects results, for De genotype in this experiment, in a yield potential of normal (hybrid) seeds around 25% of total seeds (normal+De) which is exactly the frequency expected working with a ratio of 3 De pollen for 1 normal pollen.

Therefore, increasing the quantity of normal pollen grains carried by bees by changing the female/male plant ratio will increase the hybrid seed yield produced on De female plants.

2.2.2 Seed lots got from industrial seed extraction.

Cleaning process effectiveness for seed produced on B69 genotype

Results obtained at each step of the cleaning process are summarized in Table 10.

TABLE 10

Weight (in grammes) at each step of the cleaning process of seed lots produced on B69 genotype and collected at different harvest dates

| Weight of seeds (g) | | Harvest date | | | |
|---|---|---|---|---|---|
| | | 04/08 | 08/08 | 11/08 | 19/08 |
| Primary seedlot | | 2600 | 1610 | 796 | 323 |
| Waste per cleaning step | 1 | 20 | 8 | 3 | 1 |
| | 2 | 3 | 5 | 1 | 0 |
| | 3 | 295 | 270 | 32 | 1 |
| | 4 | 315 | 140 | 29 | 11 |
| | 5 | 170 | 140 | 19 | 4 |
| | 6 | 53 | 110 | 34 | 12 |
| | 7 | 45 | 24 | 19 | 7 |
| | 8 | 23 | 15 | 18 | 7 |
| Cleaned seedlot | | 1676 | 898 | 641 | 280 |

From seed lots collected during the whole harvest period on B69 plants, around 35% were discarded. Radiographs of the cleaned seed lots showed no De type seed so the current seed extraction and cleaning method totally separate full seeds from empty and De seeds.

Cleaning process effectiveness for seeds produced on 921180 male genotype.

Results obtained at each step of the cleaning process are summarized in Table 11.

TABLE 11

Weight (in grammes) at each step of the cleaning process of seed lots produced on 921180 genotype and collected at different harvest dates

| Weight of seeds (g) | | Harvest date | | |
|---|---|---|---|---|
| | | 08/08 | 11/08 | 19/08 |
| Primary seedlot | | 5800 | 4877 | 1380 |
| Waste per Cleaning step | 1 | 50 | 16 | 2 |
| | 2 | 6 | 1 | 2 |
| | 3 | 33 | 23 | 3 |
| | 4 | 30 | 10 | 21 |
| | 5 | 99 | 30 | 42 |
| | 6 | 88 | 90 | 46 |
| | 7 | 49 | 61 | 29 |
| | 8 | 26 | 50 | 26 |
| Cleaned seedlot | | 5420 | 4606 | 1206 |

Around 7% of the seeds got from 921180 fruits were eliminated during the cleaning process. Radiographs of the cleaned seed lots showed no De type seed attesting the effectiveness of the cleaning method.

3. Quality control of seed lots

Cleaned seed lots obtained from B69 and 921180 genotypes were controlled for germination capacity and genetic conformity.

For both genotypes, seed lots were differentiated according to fruit harvest dates as follows:

for B69, 4 harvest dates from 04/08 to 19/08 therefore respectively 4 seed lots N° 952, 053, 954 and 955;

for 921180, 3 harvest dates from 08/08 to 19/08 therefore respectively 3 seed lots N° 957, 958 and 959.

3.1 Protocol 3.1.1 Germination test

Germination tests were made in standard conditions by LABOSEM from FNAMS (Fédération Nationale des Agriculteurs Multiplicateurs de Semences).

3.1.2 Genetic conformity control

The aim of the genetic conformity control is to evaluate, for each seedlot, the possible % of offtype seeds i.e. the % of seeds whose genotype is different from desired-one.

In the case of F1 seed production, the possible offtype seeds are either female or male selfings. In case of harvest on the female line only, possible offtype seeds are female selfings.

Controls on genetic conformity were made either by pathological testing (when possible) or by molecular markers.

Pathological testing:

In melon, the resistance to *Fusarium oxysporum melonis* race 1 is controlled by a dominant gene called Fom-2.

B69 being susceptible and 921180 male genotype resistant, the hybrid seeds between the 2 should be resistant, selfed seeds of B69 susceptible.

*Fusarium oxysporum melonis* race 1 resistance was tested on seed lots produced on B69 according to the protocol described in Pitrat et al., 1991.

Molecular marker testing:

Control through molecular markers is possible when, at least, one marker has been identified that can make the difference between the female and male lines and the F1. Such markers were found in melon according to the following protocol.

Seeds were germinated in soil in a growth room at 22° C. during 10 days then cotyledons taken for DNA extraction.

DNA was isolated according to the protocol described in Edwards et al., 1991.

For DNA amplification, 4 10-mer primers (OPB11, OPG17, OPP01 and OPP06 from Operon Technology, Alameda, Calif., USA) were used for the polymerase chain reaction based on the protocol of Williams et al., 1990, with minor modifications as follows:

the reaction condition was 1× reaction buffer (50 mM KCl, 10 mM Tris-HCl (pH 8.3) and 0.001% (w/v) gelatin; 0.2 $\mu$M dNTP; 2.0 mM MgCl$_2$; 0.2 $\mu$M primer; 1.0 unit of Taq polymerase and 15 ng of genomic DNA. The final volume per reaction was 25 $\mu$l.

DNA was amplified by using the following programme: 94° C. for 5 minutes, 1 cycle; 92° C. for 1 minute, 35° C. for 1 minute, 72° C. for 2 minutes, 45 cycles; 72° C. for 5 minutes, 1 cycle, then followed by soaking at 10° C.

Amplified samples were loaded on 1.5% agarose gels, which were then run at 20 V/cm. Bands were visualized with ethidium bromide and the gels were photographed under UV with polaroid films.

Amplified bands were named by the primer used and its size in base pairs (bp). For example, OPP01-1800 refers to the 1800 bp band amplified by primer OPP01.

This OPP01-1800 band, as represented in FIG. 3, was present in the male parental line and the hybrid and absent in the female line B69, therefore can be used as a suitable marker for detection of female selfings among hybrid seeds. Also marker OPP06-1100 can be used for the same purpose.

For detection of hybrids in selfings of the male parental line, 2 markers were used, OPB11-550 and OPG17-860, which both are present in the female line and the hybrid but absent in the male parental line (see illustration in FIG. 4).

3.2 Results 3.2.1 Cleaned seed lots produced on B69 genotype

Germination

Results are described in Table 12.

TABLE 12

| germinative power (in terms of % of seedlings with normal development) of the 4 cleaned seed lots produced on B69 | | | | |
|---|---|---|---|---|
| Development | Seed lots N° | | | |
| of seedlings | 952 | 953 | 954 | 955 |
| None (death) | 7 | 7 | 3 | 3 |
| Abnormal | 4 | 2 | 5 | 2 |
| Normal | 89 | 91 | 92 | 95 |

The mean germinative power of seeds collected on B69 exceeded 91% what is satisfactory.

Genetic conformity

*Fusarium oxysporum melonis* race 1 resistance test

Results are gathered in Table 13.

TABLE 13

| *Fusarium oxysporum melonis* race 1 resistance of the 4 cleaned seed lots produced on B69 (300 seeds studied per seed lot) | | | | |
|---|---|---|---|---|
| | Seed lots N° | | | |
| Number of seedlings | 952 | 953 | 954 | 955 |
| Resistant | 293 | 295 | 297 | 297 |
| Susceptible | 6 | 4 | 3 | 2 |
| Total analysed | 299 | 299 | 300 | 299 |

At maximum, 2% of selfings were evidenced among hybrid seeds produced on B69. Totalizing the results obtained during the whole harvest period, so for all seed lots, gave a mean frequency of selfings about 1.25±0.56 per 100 analysed seeds.

Molecular marker test

Results are summarized in Table 14.

TABLE 14

| Molecular marker test of the 4 cleaned seed lots produced on B69 (300 seeds studied per seed lot) | | | | |
|---|---|---|---|---|
| Molecular profile | Seed lots N° | | | |
| of seedlings | 952 | 953 | 954 | 955 |
| Hybrid banding | 294 | 288 | 286 | 279 |
| Female banding | 5 | 10 | 8 | 0 |
| None scoreable | 1 | 2 | 6 | 9 |
| Total analysed | 300 | 300 | 300 | 288 |

The mean frequency of selfings revealed by molecular marker test is about 1.93±1.46 per 100 analysed seeds.

3.3% at maximum of selfings as recorded in hybrid seed lot N° 953 means that 3.3% of the normal seeds came from fertilization with De B69 pollen where the genetic male gametophytic factor was not expressed. Therefore, among the 25% of pollen grain population which gave normal seeds (cf. Table 9), 0.8% were De pollen. Consequently, the frequency of non-expression of the genetic male gametophytic factor in this experiment was, at maximum, about 0.8/75.8=1.05% which is very close to the 1% of De-reverse events described in case of B69 selfprogenies got in summer season.

3.2.2 Cleaned seed lots produced on 921180 male genotype
Germination
Results are described in Table 15.

TABLE 15

Germinative power (in terms of % of seedlings with normal development) of the 3 cleaned seed lots got from 921180

| Development | Seed lots N° | | |
|---|---|---|---|
| of seedlings | 957 | 958 | 959 |
| None (death) | 6 | 0 | 1 |
| Abnormal | 2 | 1 | 1 |
| Normal | 92 | 99 | 98 |

The mean germinative power of seeds collected on 921180 exceeded 96% what is satisfactory.
Genetic conformity test using molecular markers
Results are summarized in Table 16.

TABLE 16

Molecular marker test of the 3 cleaned seed lots produced on 921180 (300 seeds studied per seed lot)

| Molecular profile | Seed lots N° | | |
|---|---|---|---|
| of seedlings | 957 | 958 | 959 |
| Male banding | 274 | 288 | 296 |
| Hybrid banding | 0 | 0 | 2 |
| None scoreable | 1 | 0 | 2 |
| Total analysed | 275 | 288 | 300 |

On 921180 male genotype, seed lots obtained are pure selfings except for N° 959 corresponding to last harvested seed lot from which 2 hybrid seeds per 300 analysed seeds were recorded. This can be the consequence either of De-reverse pollen or fruit mixture during harvest.

However, hypothesizing that the frequency of De-reverse event might be the same whatever the female parent (B69 or 921180), and taking into account that 921180 plants were pollinated by a pollen population containing only 15% of De pollen (cf. Table 9), the expected frequency of hybrid seeds in self seed lots of 921180 should be about $1.5/1000$ what could not be evidenced looking at 300 seeds per sampled seed lot.

4. Yield potential of hybrid seed production system using De male gametophytic factor.

In this experiment, which was conducted in optimal conditions for De embryo development (summer season), a yield of about 300 cleaned marketable hybrid seeds per m² was obtained on De female.

Hybrid seed yield between De female and normal male could be largely increased as follows:
using a prolific flowerer as pollen donor;
adapting the period of maximal fruit set on the De female to the period of male full flowering;
improving bees work i.e. effectiveness in pollen transfer;
increasing the quantity of normal pollen grains carried by bees by changing the female/male plant ratio.

Furthermore, it has been demonstrated that there was a significant seasonal effect on De embryo development i.e. in autumn or spring the capability of De embryos to reach normal development (class-1 seeds) is considerably reduced (2 to 10 times lower). Therefore, the low amount of inbred seeds (1.6%) evidenced after genetic conformity control of hybrid seed lots could be again largely reduced moving the production period from summer to autumn or spring.

Legend with FIG. 3.
Marker OPP01-1800 is indicated with an arrow.

| Lane | Sample | Individual | Marker OPP01-1800 |
|---|---|---|---|
| 1 | 952 | 259 | present |
| 2 | Molecular weight standard | | |
| 3 | 952 | 260 | absent |
| 4 | 952 | 261 | present |
| 5 | 952 | 262 | present |
| 6 | 952 | 263 | present |
| 7 | 952 | 264 | present |
| 8 | 952 | 265 | present |
| 9 | 952 | 266 | present |
| 10 | 952 | 267 | present |
| 11 | 952 | 268 | present |
| 12 | 952 | 269 | present |
| 13 | 952 | 270 | present |
| 14 | 952 | 271 | present |
| 15 | 952 | 272 | present |
| 16 | No DNA added | | |
| 17 | Female parental line B69 | | absent |
| 18 | Male parental line 921180 | | present |

Legend with FIG. 4.
Presence of marker OPG17-860 is indicated with an arrow.

| Lane | Sample | Individual | Marker OPG17-860 |
|---|---|---|---|
| 1 | Molecular weight standard | | |
| 2 | 959 | | |
| 3 | 959 | 179 | absent |
| 4 | 959 | 180 | absent |
| 5 | 959 | 181 | absent |
| 6 | 959 | 182 | absent |
| 7 | 959 | 183 | absent |
| 8 | 959 | 184 | present |
| 9 | 959 | 185 | absent |
| 10 | Female parental line B69 | | present |
| 11 | Male parental line 921180 | | absent |

REFERENCES

Edwards K., Johnstone C., Thompson C. (1991)—A simple and rapid method for the preparation of plant genomic DNA for PCR analysis—Nucleic Acids Research 19: 1349.

Jahier J. (1992)—Techniques de cytogénétique végétale—INRA Editions.

Kuckuck H., Kobabe G., Wenzel G. (1991)—Fundamentals of Plant Breeding. Springer Verlag.

Mascarhenas J. P., Stinson J. R., Willing R. P., Pe M. E. (1986)—Genes and their expression in the male gametophyte of flowering plants. In: Mulcahy D. L., Bergamini-Mulcahy G., Ottaviano E. (Eds)—Biotechnology and ecology of pollen. Springer, N.Y., pp; 39–44.

Mascarhenas J. P. (1990)—Gene activity during pollen development—Ann Rev Plant Physiol. 41: 317–338.

Meinke D. W. (1982)—Embryo-lethal mutants of *Arabidopsis thaliana:* evidence for gametophytic expression of the mutant genes—Theor Appl Genet 63: 381–386.

Meinke D. W. (1985)—Embryo-lethal mutants of *Arabidopsis thaliana:* analysis of mutants with a wide range of lethal phases. Theor Appl Genet 69: 543–552.

Meinke D. W., Baus A. D. (1986)—Gametophytic gene expression in embryo-lethal mutants of Arabidopsis thaliana—In: Mulcahy D. L., Bergamini—Mulcahy G, Ottaviano E (eds) Biotechnology and ecology of pollen—Springer, N.Y., pp 15–20.

Monnier M. (1980)—Contribution de la culture de l'embryon zygotique à la connaissance du développement et de la physiologie de l'embryon in situ—Bull Soc Bot Fr 127: 59–70.

Mulcahy D. C. (1971)—A correlation between gametophytic and sporophytic characteristics in Zea mays—Science 171: 1155–1156.

Murashige T., Skoog F. (1962)—A revised medium for rapid growth and bio-assay with tobacco tissue cultures. Physiol. Plant., 15: 473–497.

Neuffer M. G., Sheridan W. F. (1980)—Defective kernel mutants of maize. I. Genetic and lethality studies—Genetics 95: 929–944.

Ottaviano E, Sari-Gorla M, Mulcahy D. L. (1980)—Pollen tube growth rate in Zea mays: implications for genetic improvement of crops—Science 210: 437–438.

Ottaviano E, Petroni D., Pe M. E. (1988)—Gametophytic expression of genes controlling endosperm development in maize—Theor Appl Genet, 75: 252–258.

Pelletier G., Chupeau Y. (1984)—Plant protoplast fusion and somatic plant cell genetics. Physiologie végétale, 22: 377–399.

Pitrat M., Risser G., Epinat C., Ferrière C., Ricard M., Olivier C., Ruffinato A. (1991)—Techniques d'inoculation artificielle du melon avec différents agents pathogènes pour la sélection de variétés résistantes—INRA Report.

Ryczkowski M. (1967)—Osmotic gradients in the developping ovule and embryo. Acta Soc Bot Polon 36: 627–638.

Sauton A., Dumas de Vaulx R. (1987)—Obtention de plantes haploïdes chez le melon (Cucumis melo L.) par gynogénèse induite par du pollen irradié—Agronomie, 1987, 7 (2), 141–148.

Sauton A. (1988a)—Effect of season and genotype on gynogenetic haploid production in muskmelon, Cucumis melo L.—Scientia Horticulturae, 35: 71–75.

Sauton A. (1988b)—Doubled haploid production in melon (Cucumis melo L.)—Eucarpia cucurbits—31/05, 01-02/06—Montfavet, France, p. 119–128.

Sauton A., Olivier C., Chavagnat A. (1989)—Use of soft X-ray technique to detect haploid embryos in immature seeds of melon—Acta Hort. 253: 131–135.

Williams J. G. K., Kubelik A. R., Livak J. L., Rafalski J. A., Tingey S. V. (1990)—DNA polymorphims amplified by arbitrary primers are useful as genetic markers—Nucleic Acids Research 18: 6531–6535.

We claim:

1. A method of producing plants having a defective endosperm phenotype in a cucurbitacene species, the method comprising the steps of
    a. providing source plants from a cucurbitacene species;
    b. removing pollen from said plants;
    c. irradiating said pollen using gamma rays;
    d. pollinating said plants with the irradiated pollen to produce seeds containing haploid embryos;
    e. collecting the seeds resulting from said pollination;
    f. detecting haploid embryos in said seeds;
    g. regenerating and doubling the chromosome number of said haploid embryos into double haploid plants;
    h. self-crossing the doubled haploid plants to produce seeds;
    i. collecting separately, a seed lot of each doubled haploid plant resulting from said self-crossing;
    j. screening said seed lots with x-rays to differentiate between seeds having normal embryos with superposed and puffed cotyledons and seeds having embryos with spread and thin cotyledons, a characteristic of a defective endosperm phenotype;
    k. selecting and recovering seeds of plants having a homozygous defective endosperm phenotype.

2. The method of claim 1 further comprising the step of regenerating the seeds of step k into plants having a defective endosperm phenotype.

3. The method of claim 1 wherein the source plants are melon (Cucumis melo) plants.

4. The method of claim 2 wherein the source plants are derived from melon (Cucumis melo) seeds deposited with the NCIMB and assigned number 40602.

5. A method of selecting plants having a homozygous defective endosperm phenotype wherein the defective endosperm phenotype is conferred to said plants by a male gametophytic factor, the method comprising the steps of:
    a) crossing each of the plants produced by the method of claim 1 as a male parent with all other defective endosperm phenotype plants produced by the method of claim 1 as a female parent to produce hybrid seeds;
    b) collecting the hybrid seeds produced by each of the female parents resulting from the cross in step a);
    c) screening said hybrid seeds using x-rays to identify seeds having spread and thin cotyledons, a characteristic of a defective endosperm phenotype;
    d) selecting the male parent plants of step a) which produce hybrid seeds having a defective endosperm phenotype when crossed with each of the female parent plants of step a), wherein said male plants contain the male gametophytic factor for producing defective endosperm phenotype.

6. A method for producing cucurbitacene hybrid seeds using plants containing a male gametophytic factor, the method comprising the steps:
    a) crossing a plant containing a homozygous gametophytic factor and from a cucurbitacene species as a female parent with a plant which does not contain a male gametophytic factor and is from a cucurbitacene species as a male parent to produce hybrid seeds;
    b) collecting said seeds produced by the female parent;
    c) screening said seeds using x-rays and differentiating between hybrid seeds having normal embryos with superposed and puffed cotyledons and non-hybrid seeds having embryos with spread and thin cotyledons; and
    d) recovering the hybrid seeds having normal embryos.

7. The method of claim 6 wherein the hybrid seeds of step d) are heterozygous for a male gametophytic factor.

8. The method of claim 6 further comprising the step of regenerating the hybrid seeds of step d) into plants.

9. Cucurbitacene seeds which are homozygous for a male gametophytic factor.

10. The cucurbitacene seeds of claim 9 wherein the seeds are melon (Cucumis melo) seeds.

11. Cucurbitacene seeds which are heterozygous for a male gametophytic factor.

12. The cucurbitacene seeds of claim 11 wherein the seeds are melon (Cucumis melo) seeds.

13. Plants of a cucurbitacene species comprising a male gametophytic factor which confers a defective endosperm phenotype to seeds.

14. The plants of claim 13 wherein the plants are melon (*Cucumis melo*) plants.

15. A part of a plant selected from the group consisting of: cucurbitacene seeds, pollen, explants, fruit, plant cells and protoplasts comprising a male gametophytic factor which confers a defective endosperm phenotype to cucurbitacene seeds.

16. Melon seeds containing a male gametophytic factor and defective endosperm, deposited with the NCIMB and assigned number 40602.

* * * * *

UNITED STATES PATENT AND TRADEMARK OFFICE
CERTIFICATE OF CORRECTION

PATENT NO. : 6,051,752
DATED : April 18, 2000
INVENTOR(S) : Sauton et al.

It is certified that error appears in the above-identified patent and that said Letters Patent is hereby corrected as shown below:

Title page item [73], under "Assignee", delete "Petouluis Recherche France, Nimes, France" and insert --Seminis Vegetable Seed, Inc., Saticoy, California--

Signed and Sealed this

Fifteenth Day of August, 2000

Attest:

Q. TODD DICKINSON

Attesting Officer

Director of Patents and Trademarks